(12) United States Patent
De Cillis et al.

(10) Patent No.: US 6,200,989 B1
(45) Date of Patent: Mar. 13, 2001

(54) 2-ALKYLIDENE HYDROXYCUMARANONE DERIVATIVES

(75) Inventors: Gianpiero De Cillis; Roberto Di Domenico, both of Milan; Bernhard Könic, Berg; Ambrogio Oliva, Saronno VA, all of (IT)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/401,403

(22) Filed: Sep. 22, 1999

Related U.S. Application Data

(63) Continuation of application No. 09/121,458, filed on Jul. 23, 1998, now abandoned.

(30) Foreign Application Priority Data

Jul. 31, 1997 (EP) ................................. 97113190
Apr. 16, 1998 (EP) ................................. 98106946

(51) Int. Cl.[7] ................. A61K 31/4525; A61K 31/496; C07D 307/83; C07D 405/12; A61P 35/00
(52) U.S. Cl. ................. 514/320; 514/254.11; 514/470; 544/368; 546/196; 549/466
(58) Field of Search ............................. 546/196; 544/368; 549/466; 514/320, 253, 470, 254.11

(56) References Cited

U.S. PATENT DOCUMENTS

| 4,427,680 | 1/1984 | Friebe et al. ................. 424/258 |
| 4,486,442 | 12/1984 | Friebe et al. ................. 424/267 |
| 5,747,458 | * 5/1998 | Rosenberg ..................... 514/18 |

FOREIGN PATENT DOCUMENTS 0 013 894   8/1980 (EP) .
WO 86/01212  2/1986 (WO) .

OTHER PUBLICATIONS

Danoe, et al., The Receptors for Urokinase Plasminogen Activator: Stromal Cell Involvement in Extracellular Proteolysis During Cancer Invasion (Jan./1993) pp.239–245.
S.A. Rabbani, et al. J. Biol. Chem. vol. 267, pp. 14151–14156 (1992).
M. Plough, et al., J. Biol. Chem. vol. 268, pp. 17539–17546 (1993).
Goodson, et al. PNAS, vol. 91, pp. 7129–7133 (1994).
Stratton–Thomas et al. Prot. Eng. vol. 85(5) pp. 463–470 (1995).
J. Am. Chem. Soc. vol. 61, pp. 2328–2329 (1939).
Rettenberger, et al. Biol. Chem. Hoppe–Seyler vol. 376, pp. 587–594 (1995).

* cited by examiner

*Primary Examiner*—Evelyn Mei Huang
(74) *Attorney, Agent, or Firm*—George W. Johnston; Patricia S. Rocha-Tramaloni; Robert A. Silverman

(57) ABSTRACT

Compounds of the formula

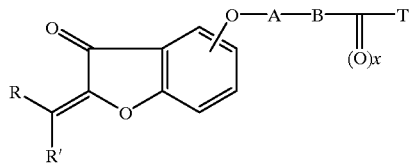

wherein R,R', A,B,T and x have the meaning given in the specification possess uPA (urokinase-type plasminogen activator) antagonist activity and can be employed as antitumor and/or antimetastatic agents.

23 Claims, No Drawings

2-ALKYLIDENE HYDROXYCUMARANONE DERIVATIVES

This is a continuation of application Ser. No. 09/121,458, filed Jul. 23, 1998, abandoned.

FIELD OF THE INVENTION

The invention relates to derivatives of 2-alkylidene hydroxycumaranones wherein the hydroxy group is substituted by a nitrogen-containing residue. These compounds possess uPA-uPAR antagonist activity and are useful as anti-tumor and/or antimetastatic agents.

BACKGROUND OF THE INVENTION

The serine proteases uPA (urokinase-type plasminogen activator) catalyzes the activation of plasminogen to plasmin which is involved in a variety of physiological and pathological processes. uPA is a multi-domain protein having a catalytic "B" chain (amino-acids 144–411) and an amino-terminal fragment ("ATF", aa 1–143) comprised of a growth factor-like domain (aa 4–43) and a kringle domain (aa 47–135). uPA is a multifunctional protein involved in tissue proteolysis, cellular migration, cellular proliferation and growth factor activation. uPA is released from cells as a virtually inactive pro-enzyme, pro-uPA. The activation of the single-chain pro-uPA by plasmin (leading to the active two-chain form) is regulated by tight control mechanisms which are not completely understood yet. Most of the uPA activities are confined to the cell surface and the pericellular environment. This is accomplished by binding to a specific, high-affinity receptor on the cell surface (uPAR). Both forms of uPA bind to uPAR with similar affinity. The binding interaction is mediated by the growth factor-like domain [S. A. Rabbani et al., J. Biol. Chem., 267, 14151–56, 1992].

The uPA receptor is a three domain glycoprotein where each triplicated motif comprises a cysteine rich consensus sequence of approximately 90 amino acids [M. Plough et al., J. Biol. Chem., 268, 17539–46, 1993]. uPAR is anchored to cell membrane by a glycosyl-phosphatidylinositol moiety (GPI anchor). uPAR binds uPA with KD values between 10-10 and 10-9 M, depending on the experimental system. The major determinants for uPA binding are located in the N-terminal domain 1. uPAR can be cleaved by uPA and plasmin, liberating a water soluble domain 1 and by the action of phospholipase C, three domains uPAR (1+2+3) can be released from the cell surface. This latter form of uPAR is also water soluble because the GPI-anchor is missing.

The inhibition of uPA dependent phenomena can principally be approached in two ways, either by direct inhibition of the proteolytic activity or by inhibition of uPA receptor binding. The latter strategy has the potential of achieving greater specificity since inhibition might be localized to the pericellular environment.

Bacteriophage display technique and protein engineering have recently been used to discover peptidic and species-specific uPAR antagonists [Goodson et al., PNAS, 91, 7129, 1994; Stratton-Thomas et al., Prot. Eng., 5, 463–470, 1995, respectively].

The uPA/uPAR system has been shown to be implicated in a variety of invasive biological processes such as tumor metastasis, trophoblast implantation, inflammation and angiogenesis. Therefore, uPAR antagonists block tumor invasiveness, metastasis and angiogenesis. Formulations containing uPAR antagonists represent therapeutic treatments for a number of highly invasive and metastasizing cancers where uPA and uPAR have been found to be consistently present at the invasive foci of the tumor [Dano et al., Proteolysis and Protein Turnover, eds. Barret+Bond, Portlan Press, 1994, London] (e.g. breast, lung, colon, ovarian cancers). In patients with breast cancer and non-small cell lung cancer increased levels of uPAR in plasma have been detected. Therefore, the amount of soluble uPAR appears to reflect the degree of proteolysis in the tumor and this might be closely related to patient prognosis. Both uPA and uPAR levels in tumor tissue are prognostic factors in many types of cancers.

In addition to cancer, other diseases mediated by cell-surface activity of uPA are addressed by uPAR antagonists. Inhibitors of plasmin generation by receptor bound uPA therefore have mechanism-based tumoristatic, anti-invasive, anti-metastatic, anti-angiogenic, anti-arthritic, anti-inflammatory, anti-osteoporotic, anti-retinopathic and contraceptive activities.

We have now discovered that derivatives of 2-alkylidene hydroxycumaranones wherein the hydroxy group is substituted by a nitrogen-containing residue have a significant activity of inhibition of the uPA/uPAR system functions by antagonizing the uPA receptor. These compounds are useful as antitumor and antimetastatic agents.

Some 6- and 4-piperidinoalkyloxy-2-alkylidenecumaranones are disclosed in EP 0 088 986 as antihistaminic agents and as inhibitors of the anaphylactic shock. No antitumor or antimetastatic activity of those compounds has been reported so far.

BRIEF DESCRIPTION OF THE INVENTION

In one aspect, the invention relates to a method of treating a solid tumor, or metastases thereof, comprising administering to a host in need of such treatment an effective amount of a compound of the formula (I):

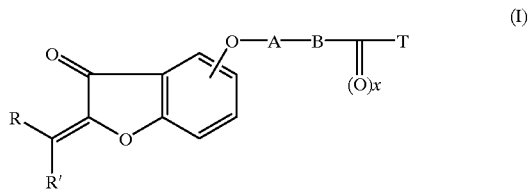

wherein:
R and R' are independently hydrogen, $C_{1-6}$-alkyl, styryl or $C_{3-6}$-cycloalkyl or, taken together with the carbon to which they are linked, form a $C_{3-6}$-cycloalkyl group;
x is 0 or 1;
A is —$(CH_2)_n$—, —$CH_2CH=CHCH_2$—, —$CH_2$—CH=CH—CH=CH—$CH_2$—, —$CH_2$—CH=CH—$CH_2$—$CH_2$—, —$CH_2$—$CH_2$—CH=CH—$CH_2$—, —$CH_2$—CH=CH—$CH_2$—$CH_2$—$CH_2$—, —$CH_2$—$CH_2$—CH=CH—$CH_2$—$CH_2$—, —$CH_2$—$CH_2$—$CH_2$—CH=CH—$CH_2$—, —$CH_2$—CHOH—CHOH—$CH_2$—, —$(CH_2)_q$—O—$(CH_2)_q$—, or —$CH_2$—A'—$CH_2$—, wherein q is an integer from 2 to 3 and n is an integer from 2 to 6, and A' is a $C_{3-7}$cycloalkyl group;
B is
(i) —$N(R^1)$—$(CH_2)_m$—$N(R^2)$—, in which m is an integer from 2 to 6, $R^1$ is hydrogen, methyl, ethyl, propyl, or isopropyl, and $R^2$ is $C_{1-6}$-alkyl, benzyl, phenyl, naphtyl or indanyl, unsubstituted or substituted by chlorine, bromine, iodine, fluorine, $C_{1-6}$—alkyl, hydroxy, amino, carboxy, $C_{1-4}$-alkoxy, $C_{1-4}$-mono- or di-alkyl amino, $C_{1-4}$—alkoxycarbonyl, mercapto, $C_{1-4}$-alkylthio; or

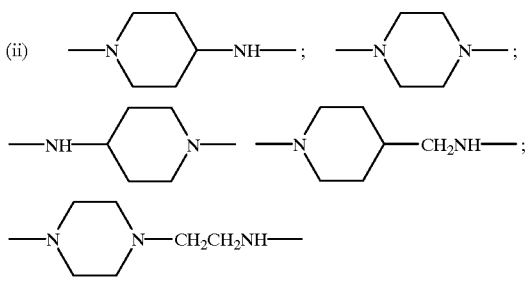

T is —CH$_2$—C≡CH, —C≡CH, —(CH$_2$)$_p$—R$^3$, —CH=CH—R$^3$, —CH$_2$—NHCO—R$^3$, —(CH$_2$)$_p$—O—R$^3$, or —CH(NH$_2$)—CH$_2$R$^3$, in which p is 0 or an integer from 1 to 4, R$^3$ is phenyl, naphthyl or biphenyl, unsubstituted or substituted by chlorine, bromine, iodine, fluorine, (C1–C6)alkyl, cyano, nitro, mono- or polyfluoroalkyl, —SO$_2$(C$_{1-4}$)alkyl, —SO$_2$NH$_2$, —SO$_2$NH(C$_{1-4}$)alkyl, —SO$_2$N[(C$_{1-4}$)alkyl]$_2$, —CONH$_2$, —CONH(C$_{1-4}$)alkyl, hydroxy, amino, carboxy, C$_{1-4}$-alkoxy, (C$_{1-4}$)mono- or di-alkyl amino, (C$_{1-4}$)alkoxycarbonyl, mercapto, or C$_{1-4}$alkylthio, or is a 5- or 6-membered heterocycle which contains 1 or 2 heteroatom(s) selected from oxygen, sulfur or nitrogen and which is or is not benzocondensed, or an enantiomer, diastereoisomer, or racemate of a compound of formula I, or a mixture thereof, or a pharmaceutically acceptable salt of a compound of formula I.

Preferably, the O-substituted residue on the cumaranone ring is in the 4 position.

In another aspect, the invention relates to a compound of formula IA

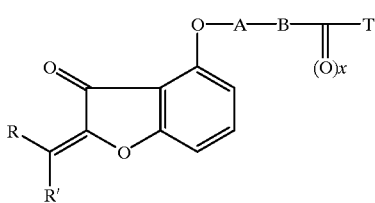

wherein R, R', x, A, B, and T are as above, provided the compound of formula IA is not 4(3-(4-(4-fluorobenzamido)piperidin)propoxy)-2-isopropylidencumaran-3-one.

Preferably, A is a —(CH$_2$)$_n$— group and n is an integer from 2–6, —CH$_2$CH=CHCH$_2$—, or —(CH$_2$)$_q$—O—(CH$_2$)$_q$— and q is an integer from 2 to 3.

Preferably, x is 1.

Preferably, B is the moiety

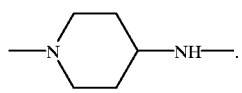

Preferably, T is phenyl or phenyl substituted by one or two trifluoro, bromo, chloro, fluoro, cyano, nitro, methyl or aminosulfonyl groups.

Preferably, R and R' are C$_{1-6}$-alkyl.

More preferably, x is 1, and B is the moiety

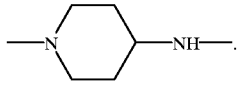

Even more preferably, when R and R' are C$_{1-6}$-alkyl, x is 1, and B is the moiety

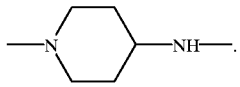

Even more preferably, when R and R' are C$_{1-6}$-alkyl, x is 1, and B is the moiety

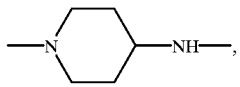

A is a —(CH$_2$)$_n$- group and n is an integer from 2–6, —CH$_2$CH=CHCH$_2$—, or —(CH$_2$)$_q$—O—(CH$_2$)$_q$— and q is an integer from 2 to 3, and T is phenyl or phenyl substituted by one or two trifluoro, bromo, chloro, fluoro, cyano, nitro, methyl or aminosulfonyl groups.

Preferably, when R and R' are methyl, x is 1, and B is the moiety

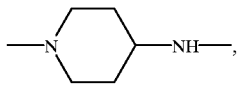

A is a —(CH$_2$)$_n$— group and n is an integer from 2–6, —CH$_2$CH=CHCH$_2$—, or —(CH$_2$)$_q$—O—(CH$_2$)$_q$— and q is an integer from 2 to 3, and T is phenyl or phenyl substituted by one or two trifluoro, bromo, chloro, fluoro, cyano, nitro, methyl or aminosulfonyl groups.

Even more preferably, when R and R' are methyl, x is 1, and B is the moiety

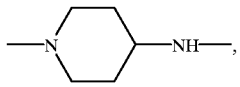

A is a —(CH$_2$)$_n$— group and n is an integer from 2–6 and most preferably from 3–4, and T is phenyl or phenyl substituted by one or two trifluoro, bromo, chloro, fluoro, cyano, nitro, methyl or aminosulfonyl groups.

Preferably, when R and R' are methyl, x is 1, and B is the moiety

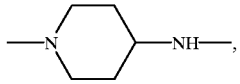

A is —CH$_2$CH=CHCH$_2$—, and T is phenyl or phenyl substituted by one or two trifluoro, bromo, chloro, fluoro, cyano, nitro, methyl or aminosulfonyl groups.

Preferably, when R and R' are methyl, x is 1, and B is the moiety

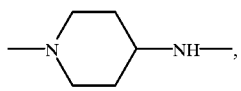

A is —(CH$_2$)$_q$—O—(CH$_2$)$_q$— and q is an integer from 2 to 3, and T is phenyl or phenyl substituted by one or two trifluoro, bromo, chloro, fluoro, cyano, nitro, methyl or aminosulfonyl groups.

DETAILED DESCRIPTION OF THE INVENTION

The invention relates to the use of the compounds of the formula (I)

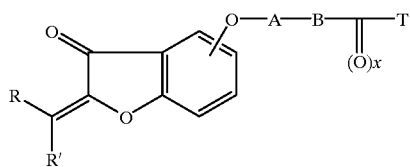

(I)

wherein:

R and R' are independently hydrogen, V$_{1-6}$-alkyl, styryl or C$_3$6-cycloalkyl or, taken together with the carbon to which they are linked, form a C$_{3-6}$-cycloalkyl group;

x is 0 or 1;

A is selected from the following groups: —(CH$_2$)$_n$—,
—CH$_2$CH=CHCH$_2$—,
—CH$_2$—CH=CH—CH=CH—CH$_2$—, —CH$_2$—CH=CH—CH$_2$—CH$_2$—, —CH$_2$—CH$_2$—CH=CH—CH$_2$—,
—CH$_2$—CH=CH—CH$_2$—CH$_2$—CH$_2$—, —CH$_2$—CH$_2$—CH=CH—CH$_2$—CH$_2$—,
—CH$_2$—CH$_2$—CH$_2$—CH=CH—CH$_2$—, —CH$_2$—CHOH—CHOH—CH$_2$—, —(CH$_2$)$_q$—O—(CH$_2$)$_q$—,
—CH$_2$—A'—CH$_2$—, wherein q is an integer from 2 to 3 and n is an integer from 2 to 6, and A' is a C$_{3-7}$-Cycloalkyl group;

B is either (i) —N(R')—(CH$_2$)$_m$—N(R$^2$)—, in which m is an integer from 2 to 6, R$^1$ is hydrogen, methyl, ethyl, propyl, or isopropyl, and R$^2$ is C$_{1-6}$-alkyl, benzyl, phenyl, naphtyl or indanyl optionally substituted by chlorine, bromine, iodine, fluorine, C$_{1-6}$-alkyl, hydroxy, amino, carboxy, C$_{1-4}$-alkoxy, C$_{1-4}$-mono- or di-alkyl amino, C$_{1-4}$-alkoxycarbonyl, mercapto, C$_{1-4}$-alkylthio; or (ii) 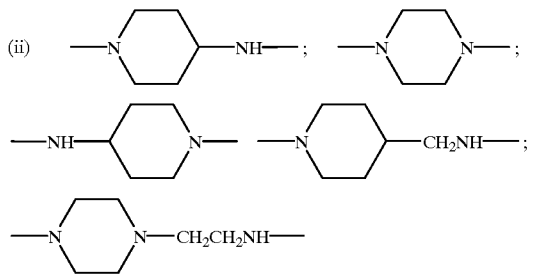

T is selected from —CH$_2$—C≡CH, —C≡CH, —(CH$_2$)$_p$—R$^3$, —CH=CH—R$^3$, —CH$_2$—NHCO—R$^3$, —(CH$_2$)$_p$—O—R$^3$, —CH(NH$_2$)—CH$_2$R$^3$, in which p is 0 or an integer from 1 to 4, R$^3$ is phenyl, naphthyl or biphenyl, optionally substituted by chlorine, bromine, iodine, fluorine, (C1–C6)alkyl, cyano, nitro, mono- or polyfluoroalkyl, —SO$_2$(C$_{1-4}$)alkyl, —SO$_2$NH$_2$, —SO$_2$NH(C$_{1-4}$)alkyl, —SO$_2$N[(C$_{1-4}$)alkyl]$_2$, —CONH$_2$, —CONH(C$_{1-4}$)alkyl, hydroxy, amino, carboxy, C$_{1-4}$-alkoxy, (C$_{1-4}$)mono- or di-alkyl amino, (C$_{1-4}$)alkoxycarbonyl, mercapto, or C$_{1-4}$-alkylthio, or is a 5- or 6-membered heterocycle which contains 1 or 2 heteroatom(s) selected from oxygen, sulfur or nitrogen and which can be benzocondensed, as well as the salts of the' compounds of formula (I) with pharmaceutically acceptable acids or bases, in the manufacture of medicaments for the treatment of tumours, particularly advanced solid tumours of breast, lung and colon, and metastases thereof.

The above formula I is understood to comprise enantiomers, diastereomers and racemates of the compounds of formula (I), and mixtures thereof which are also included within the scope of the present invention.

The term "benzocondensed" means that the heterocycle has two carbon atoms in common with a phenyl ring. Examples of 5- and 6-membered are thiophene, pyridine, and furane. Examples of benzocondensed 5- and 6-membered heterocycles are imidazole, quinoline, isoquinoline, indole, benzothiazole and benzoimidazole.

Preferred compounds of formula (I) are those in which A is a —(CH2)$_n$— group and n is an integer from 2–6, those in which B is a moiety

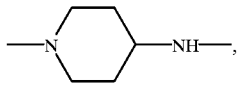

those in which x is 1, those in which T is phenyl or phenyl substituted by one or two trifluoromethyl, bromo, chloro, fluoro, cyano, nitro, methyl or aminosulfonyl groups, and those in which the O-substituted residue on the cumaranone ring is in the 4 position. Particularly preferred compounds of formula (I) are those in which R and R' are both methyl.

The most preferred compounds are:
4-(4-(4-(3,4-dichlorobenzamido)piperidin-1yl)butoxy)-2-isopropylidenecumaran-3-one;
(E)-4-(4-(4-(3,4-dichlorobenzamido)piperidin-1-yl)-2-butenoxy)-2-isopropylidenecumaran-3-one;
(Z)-4-(4-(4-(3,4-dichlorobenzamido)piperidin-1-yl)-2-butenoxy)-2-isopropylidenecumaran-3-one;
4-(3-(4-(3-aminosulfonyl4-chlorobenzamido)piperidin-1yl) propoxy)-2-isopropylidenecumaran-3-one;
4-[(2-(2-(4-(4-fluorobenzamido)piperidin -1-yl)ethyl)oxy) ethyloxy]-2-isopropylidenecumaran-3-one.

The compounds of formula IA

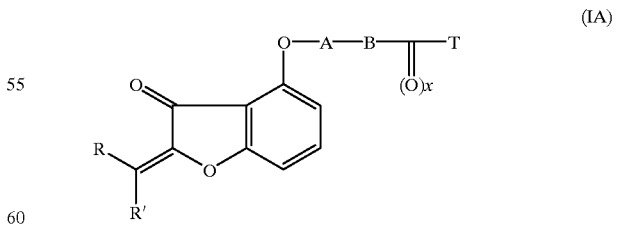

(IA)

wherein R,R', A,B,T and x are as above, their enantiomers, diastereomers, racemates and pharmaceutically acceptable salts thereof with the exception of 4(3-(4-(4 fluorobenzamido)piperidin)propoxy)-2-isopropylidencumaran-3-one are also an object of the invention.

Another object of the present invention are pharmaceutical compositions containing a pharmacologically effective amount of a compound of formula (IA) with the exception of 4(3-(4-(4-fluorobenzamido)piperidin)propoxy)-2-isopropylidencumaran-3-one in admixture with pharmaceutically acceptable excipients and/or diluents.

Preparation of the Compounds of the Invention

The compounds of formula (I) can be prepared according to the two-step process described in U.S. Pat. No. 4,486,442 (corresponding to EP 088 986), which is herein incorporated by reference, which comprises reacting an intermediate of formula (II):

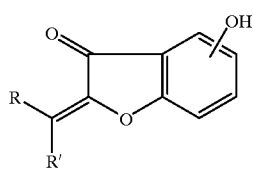
(II)

in which R and R' have the above meanings, an intermediate of formula (III):

(III)

in which A has the above meanings and L, L' are leaving groups, which can be the same or different, and are preferably selected from chlorine, bromine, iodine, mesyl or tosyl groups, and an intermediate of formula (IV):

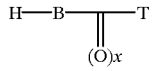
(IV)

in which B, T and x have the above meanings, said intermediates being reacted in two possible ways:

(i) reaction of a compound of formula (II) with a compound of formula (III), followed by reaction of the so obtained product with a compound of formula (IV), or alternatively reaction of a compound of formula (IV) with a compound of formula (III), followed by reaction of the so obtained product with a compound of formula (II).

In both cases the intermediate product of the first synthesis step is preferentially isolated before submitting it to the second reaction. In such a process in general the oxygen-alkylation is performed under strong basic conditions, preferably by means of an alkoxide of alkaline metal such as sodium ethoxide or isopropoxide, in a suitable solvent, preferably a $(C_{1-4})$alkyl alcohol, and at temperatures ranging from 50° C. to the boiling temperature of the solvent.

The nitrogen-alkylation is performed under milder conditions, in the presence of a base such as an organic base, preferably a trialkylamine, or an inorganic base, preferably a carbonate of an alkaline or alkaline-earth metal, at temperatures ranging from room temperature to 50° C.

The intermediates of formula (II) can be obtained from the intermediates of formula (II'):

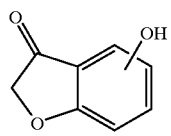
(II')

by reaction with an aldheyde or ketone of formula R—CO—R', in which R and R' are as above defined, in the presence of a base, preferably an hydroxide of an alkaline metal, in a solvent and at temperatures up to 100° C. A preferred reaction employs potassium hydroxide at reflux in ethanol.

The compounds of formula (II') are known and are described in J. Am. Chem. Soc., 61, 2328 (1939), which is herein incorporated by reference.

The intermediates of formula (III) are commercial products or can easily be prepared starting from commercial products by known methods such as halogenation of alcohols or their conversion into mesyl and tosyl derivatives.

The intermediates of formula (IV) can be prepared starting from a suitably mono-protected diamine of formula P—B—H, in which P is for example a benzyl or tert-butoxycarbonyl group, by acylation (if x=1) or alkylation (if x=0) with a compound of formula (IV'):

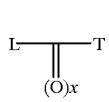
(IV')

in which L, T and x have the above meanings, preferably in the presence of a base and of an inert solvent and at temperatures ranging from 0° C. to 50° C.

Alternatively, the compounds of formula (IV) in which x=0 can be obtained from the corresponding compounds with x=1 by reduction of the amido group, for example with lithium aluminium hydride.

The mono-protected diamiines of formula P—B—H and the compounds of formula (IV') are known commercial products or can be prepared from commercial products according to known methods.

Biological Activity of the Compounds of the Invention

Compounds of the invention were tested (ELISA test) as inhibitors of human urokinase (uPA) binding to its specific receptor uPAR mAk (BIO-R4), according to the procedure described in Biol. Chem. Hoppe-Seyler, 376, 587–94 (1995) by Rettenberger et al. The assays are performed in Microtiterplates (96 wells). The following solutions are used:

washing buffer PBS-buffer (without $Mg^{2+}$ and $Ca^{2+}$)+ 0.05% Tween 20;

incubation buffer (IP): 1% skimmed milk powder in PBS-buffer (without $Mg^{2+}$ and $Ca^{2+}$);

BIO-R4 solution: 50 ng/well (0.5 (g/ml; 100 (l/well) in IP;

uPAR solution: 3 ng/well (30 ng/ml; 100 (l/well) in PBS-buffer (without $Mg^{2+}$ and $Ca^{2+}$);

blocking solution: 1% skimmed milk powder in washing buffer (dissolved at 37° C.);

uPA solution: 0.25 ng/well (5 ng/ml; 50 (l/well) in IP.

Detect ion solutions (per microtiterplate):

(1) 6 ml (100 mM Tris-Cl pH 7.2+0.15% Tween 80)+1.5 ml (10 (g) Plasminogen in aqua bidest;

(2) 6 ml (100 mM Tris-Cl pH 7.2+0.15% Tween 80)+1.5 ml (7.5 mg) chromozyme PL in aqua bidest.

The detection solution must be continuously stirred. Testing substances: the testing substances are dissolved in DMSO. They are used in the test system with a highest concentration of 100 (g/ml. The solutions are prepared using PBS.

Three controls are performed:
a) positive control: using 2% DMSO in PBS;
b) negative control: assay without receptor;
c) inhibition control:
  1) inhibition ($IC_{95}$ at 0.25 mg/ml) with dextranesulfate (MW=500.000);
  2) inhibition ($IC_{90}$ at 1 (g/ml) with inactivated uPA (175 (g/ml).

Incubation is done as follows:

Each well is incubated by 100 (1 of BIO-R4 (c=0.5 (g/ml) for 1 hour at room temperature under shaking. After washing three times with the washing buffer, each well is incubated for 1 hour (37° C.) with 200 (l/well blocking solution. After triple washing each well is incubated for 1 hour at room temperature under shaking with 100 (l/well uPAR (c=30 ng/ml), then the wells are washed again three times with the washing buffer. The testing substance solution and the control solution, respectively, are added (50 (l/well) and are incubated for 30 minutes at room temperature under shaking. An additional 50 (l of uPA solution (c=2.5 ng/ml) are added. After 1 hour at room temperature a triple washing is performed.

For detection, the following procedure is used:

Incubation with 50 (l each of detection solution (1) and (2) at room temperature. After 20 minutes a yellow colour will be visible (the positive control reads an extinction of 1 after 45–60 minutes). The detection is performed at 405 nm (reference is 490 nm) using a Dynatech MR 7000 ELISA reader. To obtain the percentage of inhibition the following formula is used (E stands for extinction):

$$\% \text{ Inhibition} = 100 - 100 \times [E_{test} - E_{neg\cdot control} / E_{pos\cdot control} - E_{neg\cdot control}]$$

The data for representative compounds of the invention are shown below

| Compound | IC50 [µg/ml] |
|---|---|
| 4-(4-(4-(3,4-dichlorobenzamido)piperidin-1-yl)butoxy)-2-isopropylidenecumaran-3-one | >0.01 |
| (E)-4-(4-(4-(3,4-dichlorobenzamido)piperidin-1-yl)-2-butenoxy)-2-isopropylidenecumaran-3-one | >0.01 |
| (Z)-4-(4-(4-(3,4-dichlorobenzamido)piperidin-1-yl)-2-butenoxy)-2-isopropylidenecumaran-3-one | >0.01 |
| 4-(3-(4-(3-aminosulfonyl-4-chlorobenzamido)piperidin-1yl)propoxy)-2-isopropylidenecumaran-3-one | 0.05 |
| 4-[(2-(2-(4-(4-fluorobenzamido)piperidin-1-yl)ethyl)oxy)ethyloxy]-2-isopropylidenecumaran-3-one | 0.05 |

The invention also concerns pharmaceutical agents containing one or more compounds of formula (I).

In order to produce pharmaceutical agents, the compounds of formula (I) are mixed in a known manner with suitable pharmaceutical carrier substances, aromatics, flavouring and dyes and are formed for example into tablets or coated tablets or they are suspended or dissolved in water or an oil such as e.g. olive oil with addition of appropriate auxiliary substances.

The substance of the general formula (I) can be administered orally or parenterally in a liquid or solid form. Water is preferably used as the medium which contains the stabilizing agents, solubilizers and/or buffers which are usually used for injection solutions. Such additives are for example tartrate or borate buffers, ethanol, dimethylsulfoxide, complexing agents (such as ethylendianinotetraacetic acid), high molecular polymers (such as liquid polyethylene oxide) for the regulation of the viscosity or polyethylene derivatives of sorbitol anhydrides.

Solid carrier substances are e.g. starch, lactose, mannitol, methylcellulose, talcum, highly dispersed silicic acid, higher molecular fatty acids (such as stearic acid), gelatin, agar-agar, calcium phosphate, magnesium stearate, animal and vegetable fats or solid high molecular polymers (such as polyethylene glycols). Suitable formulations for the oral route can if desired contain flavourings and sweeteners.

The administered dose depends on the age, the health and the weight of the patient, the extent of the disease, the type of treatments which are possibly being carried out concurrently, the frequency of the treatment and the type of the desired effect. The daily dose of the active compound is usually 0.1 to 50 mg/kg body weight. Normally 0.5 to 40 and preferably 1 to 20 mg/kg/day in one or several applications per day are effective in order to obtain the desired results.

The invention is illustrated further by the following nonlimiting examples:

Preparation 1: N-benzyl4-(4-fluorobenzamido) piperidine

A mixture of N-benzyl-4-aminopiperidine (30 g) and sodium bicarbonate (53 g) in 300 ml of dry methylene chloride was cooled to 10° C. To this solution 23.24 ml of 4-fluorobenzoyl chloride were added dropwise. After one hour at room temperature the reaction mixture was poured into 800 ml of water and extracted with chloroform (2×200 ml). The organic extracts were collected, dried over sodium sulfate and concentrated to dryness. The residue (50 g) was treated with 300 ml of diethyl ether with stirring for 2 hours, then filtered and dried under vacuum at 50° C. to give 45.8 g of the product, m.p. 163–165° C.

Preparation 2: 4-(4-fluorobenzamido)piperidine

To a solution of N-benzyl-4-(4-fluorobenzamido) piperidine (1 g) in 15 ml of dry methanol 0.2 g of palladium on charcoal followed by 1 g of ammonium formate were added. After 3 hours at room temperature the palladium on charcoal was filtered off and the mixture was concentrated to dryness. The residue was dissolved in water, brought to pH 9, and extracted with chloroform (3×20 ml). The organic extracts were collected, dried over sodium sulfate and concentrated to dryness to give 0.63 g of the product, m.p. 165–168° C.

Preparation 3: 4-hydroxy-2-isooropylidenecumaran-3-one

A mixture of 4-hydroxycumaran-3one (35 g) and potassium hydroxide (86.3 g) in 863 ml of absolute ethanol and 120 ml of dry acetone was heated to 50° C. for about 1 hour (until the suspension had completely dissolved). The reaction mixture was brought to pH 4.5 with 37% hydrochloric acid, then concentrated to a small volume. The remaining suspension was poured into 1250 ml of water, stirred for 1 hour, filtered and dried under vacuum to give 38.8 g of the product, m.p. 107–109° C.

Preparation 4: N-tertbutoxycarbonyl-3-(4-fluorobenzamido) propylamine

A mixture of N-tertbutoxycarbonyl-1,3-propylenediamine (1.74 g) in 17 ml of ethylacetate and 17 ml of saturated aqueous sodium bicarbonate solution was cooled to 0° C. To this mixture a solution of 1.31 ml of 4-fluorobenzoyl chloride in 3 ml of ethyl acetate was added dropwise. The reaction mixture was kept at room temperature overnight, then poured into 50 ml of water. The organic layer was separated and the aqueous phase extracted with ethyl acetate. The organic extracts were collected, dried over sodium sulfate and concentrated to dryness. The residue was treated with 10 ml of hexane with stirring for 1 hour, then filtered and dried under vacuum at 50° C. to give 2.84 of the product, m.p. 91–93° C.

Preparation 5: 3-(4-fluorobenzamido)propylamine

A solution of N-tertbutoxycarbonyl-3-(4-fluorobenzamido)propylamine (2.76 g; preparation 4) in 50 ml of dry methylene chloride and 7.11 ml of trifluoroacetic acid was stirred at room temperature overnight. The reaction mixture was then concentrated to dryness, redissolved in 50 ml of sodium bicarbonate solution and extracted with ethyl acetate (2×50 ml). Then the mother liquor was brought to pH 9.5, and after the addition of sodium chloride extracted again with ethyl acetate (5×100 ml). The organic extracts were collected, washed with saturated aqueous solution of sodium chloride (50 ml), dried over sodium sulfate and concentrated to dryness, to give 2.6 g of the product.

Preparation 6: N-benzyl-(4-tertbutoxycarbonylamino) piperidine

A solution of N-benzyl4-aminopiperidine (50 g) in 500 ml of tetrahydrofuran was cooled to 0° C. To this solution, a solution of ditert-butoxycarbonylether (65 g) in 65 ml of tetrahydrofuran was added dropwise. The resulting solution was concentrated to dryness, redissolved in 300 ml of chloroform and washed with 100 ml of brine, then dried over sodium sulfate and concentrated to dryness. The residue (80 g) was suspended in 160 ml of hexane and stirred at room temperature for 1 hour to give after drying under vacuum at 50° C., 72.4 g of the product, m.p. 122–124° C.

Preparation 7: 4-(tert-butoxycarbonylamino)piperidine

A mixture of N-benzyl-(4-tertbutoxycarbonylamino) piperidine (71 g), palladium on charcoal (7.1 g) and ammonium formate (78.6 g) in 1000 ml of dry methanol was stirred at room temperature overnight. The palladium on charcoal was then filtered off and the mixture concentrated to dryness and redissolved in 300 ml of water. The pH was adjusted to about 9 by the addition of 20% sodium hydroxide. The aqueous phase after the addition of sodium chloride was extracted with ethyl acetate (3×100 ml). The organic extracts were pooled and dried over sodium sulfate and the solvent evaporated under reduced pressure. The residue (70 g) was suspended in 140 ml of hexane and stirred at room temperature for 1 hour to give, after drying under vacuum at 50° C., 48 g of the product, m.p. 150–152° C.

Preparation 8: 3-[4-(tertbutoxycarbonylamino)piperidin-1-yl]-1-chloropropane

A mixture of (4-tertbutoxycarbonylamino)piperidine (20 g) and potassium carbonate (20.7 g) in 200 ml of dry dimethylformamide was cooled to 0° C. A solution of 1-bromo-3-chloropropane (11.8 ml) in 11.8 ml of dimethylformamide was added. dropwise thereto. The mixture was kept at room temperature overnight, then poured in 2000 ml of water and extracted with ethyl acetate (2×200 ml). The organic extracts were pooled, washed with 100 ml of brine, dried over sodium sulfate and concentrated to dryness. The oily residue (24 g) was crystallized from 72 ml of hexane to give 11.26 g of the product, m.p. 79–82° C. A further 4 g of the product was obtained by chromatographic purification (eluent chloroform/methanol 9:1) of the mother liquors of the crystallization.

Preparation 9: 3-(4-aminopiperidin-1-yl)-1-chloropropane 1.35 ml of 8 N solution of hydrogen chloride in ethanol was added to solution of 3-[4-(tertbutoxycarbonylamino) piperidin-1-yl]-l-chloropropane (0.5 g) in 5 ml of absolute ethanol. A precipitate quickly formed. After stirring at room temperature overnight, the solid was collected by filtration and dried under vacuum at 40° C. to give 0.4 g of the product, m.p. 266–268° C.

Preparation 10: N-benzyl-4-benzamidopiperidine

A mixture of N-benzyl-4-aminopiperidine (5 g) and sodium bicarbonate (8.83 g) in 50 ml of dry methylene chloride was cooled to 10° C. and 3.68 ml of benzoyl chloride was added dropwise thereto. After 1 hour at room temperature, the reaction mixture was poured into 100 ml of water and extracted with methylene chloride (2×100 ml). The organic extracts were pooled, dried over sodium sulfate and concentrated to dryness. The residue (10 g) was suspended in 200 ml of diethyl ether and stirred at room temperature for 2 hours to give, after drying under vacuum, 6,92 g of the product, m.p. 168–171° C.

Preparation 11: 4-benzamidopiperidine

A suspension of N-benzyl-4-benzamidopiperidine (6.62 g; preparation 10) and palladium on charcoal (1 g) in 300 ml of dry methanol was hydrogenated at 49° C. for 12 hours (about 750 ml of hydrogen were consumed), then the palladium on charcoal was filtered off. The solvent was evaporated under reduced pressure and the residue (5 g) is crystallized from 50 ml of diethyl ether and finally dried under vacuum at 50° C. 3.28 g of the product were obtained, m.p. 136–139° C.

Preparation 12: 4-hydroxy-2-(4'-heptylidene)cumaran-3-one

A mixture of 4-hydroxycumaran-3-one (1 g), potassium hydroxide (3.46 g) and 4-heptanone (6.64 ml) in 50 ml of absolute ethanol was heated to 40° C. for 4 hours and at reflux for an additional 4 hours. The reaction mixture was concentrated to dryness, redissolved in 50 ml of water and the pH adjusted to about pH 4, then extracted with chloroform (2×50 ml), The organic extracts were pooled, dried over sodium sulfated and concentrated to dryness. The residue (1.8 g of a red oil) was purified by silica gel chromatography (eluent hexanelethyl acetate 5:1) to give 1.04 g of the product as a red oil.

Preparation 13: N-benzyl-4-acetamidopiperidine

A mixture of N-benzyl-4-aminopiperidine (5 g) and sodium bicarbonate (8.83 g) in 50 ml of dry methylene chloride was cooled to 10° C. 2.32 ml of acetyl chloride were added dropwise. After 1 hour at room temperature, the mixture was poured into 100 ml of water and extracted with methylene chloride (3×100 ml). The organic extracts were pooled, dried over sodium sulfate and concentrated to dryness to give, after crystallization from 30 ml of diethyl ether, 5.09 g of the product, m.p. 140–143° C.

Preparation 14: 4-acetamidopiperidine

A mixture of N-benzyl4-acetamidopiperidine (4.89 g; preparation 13) and 0.3 g of palladium on charcoal in 150 ml of methanol was hydrogenated for 4 hours (about 600 ml of hydrogen were consumed), then the palladium on charcoal was filtered off. The reaction mixture was concentrated to dryness and the residue crystallized from 50 ml of diethyl ether to give 2.54 g of the product, m.p. 130–133° C.

Preparation 15: N-benzyl4heptanoylaminopiperidine

A mixture of N-benzyl-4-aminopiperidine (10 g) and sodium bicarbonate (17.65 g) in 50 ml of dry methylene chloride was cooled to 10° C. Then, 9.85 ml of heptanoyl chloride were added dropwise. The reaction mixture was kept at room temperature for 1 hour, then slowly added to 500 ml of water. The organic phase was separated and washed with 200 ml of water, dried over sodium sulfate and concentrated to dryness. The residue (15 g) was crystallized from 60 ml of diethyl ether to give 11.5 g of the product, m.p. 92–95° C.

Preparation 16: 4-heptanoylaminopiperidine

A mixture of N-benzyl-4-heptanoylpiperidine (11 g; preparation 15) and pylladium on charcoal (0.55 ml) in 165 ml of dry methanol was hydrogenated at 50° C. for about 3 hours 30 minutes (about 800 ml of hydrogen were consumed), then the catalyst was filtered off and the reaction mixture was concentrated to dryness, to give 7.6 g of the product, m.p. 75–77° C.

Preparation 17: 4-hydroxy-2-cyclopentylidenecumaran-3-one

A mixture of 4-hydroxycumaran-3-one (1.5 g), potassium hydroxide (3.7 g) and cyclopentanone (6.24 ml) in 37 ml of absolute ethanol was heated to 40° C. for 2 hours, then kept at room temperature overnight. The pH was then adjusted to pH 4 and the solvent evaporated under reduced pressure. 100 ml of water were added to the residue and the mixture extracted with ethyl acetate (2×50 ml). The organic extracts were pooled, dried over sodium sulfate and concentrated to dryness. The residue (10 g of a red oil) was treated with 50 ml of water to form a solid which was separated by decantation and treated again with 50 ml of water, then with 10 ml of ethanol. The solid was finally recovered by filtration and dried under vacuum, to give, after recrystallization from 18 ml of hexane and purification by silica gel chromatography (eluent hexane/ethyl acetate 10:1), 0.89 g of the product.

Preparation 18: N-benzyl-4-cyclohexylamidopiperidine

A mixture of N-benzyl-4-aminopiperidine (20 g) and sodium bicarbonate (35.3 g) in 200 ml of dry methylene chloride was cooled to 10° C. 17.2 ml of cyclohexanecarbonyl chloride were added dropwise. After 1 hour at room temperature, the reaction mixture was poured into 300 ml of water, the organic phase separated and washed with 100 ml of water, dried over sodium sulfate and concentrated to dryness. The residue (35 g) was crystallized from 200 ml of diethyl ether and dried under vacuum at 50° C., to give 26.6 g of the product, m.p. 150–152° C.

Preparation 19: 4-cyclohexylamidopiperidine

A mixture of N-benzyl-4-cyclohexylamidopiperidine (20 g; preparation 18) and palladium on charcoal (1 g) in 300 ml of dry methanol was hydrogenated for 6 hours (about 2000 ml of hydrogen were consumed), then the catalyst was filtered off and the solvent was evaporated under reduced pressure. The residue (14 g) was crystallized from 60 ml of diethyl ether to give 12.7 g of the product, m.p. 174–176° C.

Preparation 20: 4-hydroxy-2-cyclohexylidenecumaran-3-one

A mixture of 4-hydroxycumaran-3-one (6.16 g), potassium hydroxide (6.16 g) and cyclohexanone (12 ml) in 75 ml of ethanol 96% was heated to 50° C. for 2 hours, then the mixture was concentrated to dryness, 200 ml of water were added and the pH adjusted to pH 2 by the addition of hydrochloric acid (37%). The mixture was extracted with methylene chloride (3×100 ml), the organic extracts pooled, washed with 100 ml of water, dried over sodium sulfate and concentrated to dryness. The residue (5 g of a red oil) was purified by silica gel chromatography (eluent methylene chloride/hexane 5:1) to give, after crystallization from 20 ml of hexane and drying under vacuum at 30° C., 1.72 g of the product, m.p. 117–120° C.

EXAMPLE 1

3-[4-(4-fluorobenzamido) piperidinyl]-1-chloropropane

A mixture of 10.65 g of 4-(4-fluorobenzamido)piperidine (preparation 2) and potassium carbonate (9.93 g) in 160 ml of dry dimethylformamide was cooled to 0° C. and a solution of 1-bromo-3-chloropropane (5.68 ml) in 5.68 ml of dry dimethylformamide added dropwise thereto. After 3 hours at room temperature the reaction mixture was poured into 1600 ml of water and stirred for one hour. The solid which precipitated was recovered by filtration (7.1 g).

The mother liquors were extracted with ethyl acetate (2×100 ml), then adjusted to pH 9–10 and extracted again with chloroform (3×100 ml). The organic extracts were collected, dried over sodium sulfate and concentrated to dryness to give 5 g of a solid, which was added to the 7.1 g recovered before. The solid material was treated overnight with 50 ml of ethyl acetate with stirring, filtered and dried under vacuum to give 4 g of the product.

EXAMPLE 2

4-[3-(4-(4-fluorobenzamido)piperidin)propoxy]-2-isopropylidenecumaran-3-one

A suspension of sodium metal (0.8 g) in 300 ml of anhydrous isopropanol was heated to 60° C. until all of the sodium was solubilized (about 2 hours 30 minutes), then 5.78 g of 4-hydroxy-2-isopropylidene cumaran-3-one (preparation 3) were added and the mixture was refluxed for 1 hour. 3-[4-(4-fluorobenzamido) piperidinyl]-1-chloropropane (10 g; example 1) was added and the reaction mixture refluxed for 3 hours, then kept at room temperature overnight.

The mixture was concentrated to a small volume (about 50 ml) then 1000 ml of water were added and the pH brought to 9. The resulting basic mixture was extracted with chloroform (3×300 ml) and the organic extracts collected, dried over sodium sulfate and concentrated to dryness. The residue of 13.8 g was treated with diethyl ether (138 ml) with stirring and at reflux for 30 minutes, then filtered and purified by silica gel chromatography (eluent chloroform/methanol 9:1) to give 9.3 g of the product, m.p. 188–190°C.

The product was converted to the hydrochloride by treatment of an ethanol solution with a 5.5 M solution of hydrogen chloride in ethanol and precipitation from diethyl ether. M.p. of the hydrochloride 235–238° C.

EXAMPLE 3

4-(3-chloropropoxy)-2-isopropylidenecumaran-3-one

A mixture of 4-hydroxy-2-isopropylidenecumaran-3-one (19.2 g; preparation 3), potassium carbonate (13.95 g) and 1-bromo-3-chloropropane (11.8 ml) in 250 ml of dry dimethylformamide was heated to 50° C. for 3 hours, then the reaction mixture was poured into 2500 ml of water and extracted with chloroform (3×100 ml). The organic extracts were collected, washed with saturated aqueous solution of sodium chloride (100 ml), dried over sodium sulfate and concentrated to dryness.

The residue (28 g) was purified by silica gel chromatography (eluent methylene chloride) to give, after drying under vacuum at 40° C., 19.36 g of the product, m.p. 78–80° C.

EXAMPLE 4

4-[3-(3-(4-fluorobenzamido)propylamino)propoxy]-2-isopropylidenecumaran-3-one

A mixture of 4-(3-chloropropoxy)-2-isopropylidenecumaran-3-one (1.69 g; example 3), 3-(4-fluorobenzamido)propylamine (2 g; preparation 5) and potassium carbonate (0.88 g) in 50 ml of dry dimethylformamide was heated to 50° C. overnight, then the reaction mixture was poured into 500 ml of water and extracted with ethyl acetate (3×100 ml). The organic extracts were collected, washed with 50 ml of water, dried over sodium sulfate and concentrated to dryness. The residue (3 g) was purified by silica gel chromatography (eluent: chloroform/methanol 9:1) to give 0.11 g of the product.

EXAMPLE 5

4-(3-piperazinopropoxy)-2-isopropylidenecumaran-3-one

A suspension of piperazine (5.47 g) in 42 ml of dry dimethylformamide was heated to 50° C. until the solid had completely dissolved, then the reaction mixture was cooled to room temperature. 2.84 g of 4-(3-chloropropoxy)-2-isopropylidenecumaran-3-one (example 3) were added. After 1 day of stirring the mixture was poured into 420 ml of water and extracted with ethyl acetate (2×100 ml) and chloroform (2×φml), dried over sodium sulfate and concentrated to dryness.

The residue (3.3 g) was purified by silica gel chromatography (eluent: chloroform/methanol/ammonium hydroxide 80:20:1), to give 2.87 of the product as a red oil.

EXAMPLE 6

4-[3-(4-(4-fluorobenzamido)piperazin)propoxy]-2-isopropylidenecumaran-3-one

A mixture of 4-(3-piperazinopropoxy)-2-isopropylidenecumaran-3-one (0.318 g; example 5), 4-fluorobenzoyl chloride (0.156 ml) and saturated aqueous sodium bicarbonate solution (5 ml) in 5 ml of dry methylene chloride was stirred for 2 hours at room temperature. The organic phase was separated, dried over sodium sulfate and concentrated to dryness. The residue (0.47 g) was crystallized from diethyl ether/hexane to give 0.274 g of the product, m.p. 97–99° C.

EXAMPLE 7

4-(4-chlorobutoxy)-2-isopropylidenecumaran-3-one

A mixture of 4-hydroxy-2-isopropylidenecumaran-3-one (0.56 g; preparation 3), 1-bromo-4-chlorobutane (0.41 ml) and potassium carbonate (0.4 g) in 10 ml of dry dimethylformamide was heated to 50° C. for 3 hours. The reaction mixture was then poured into 100 ml of water and, after the addition of sodium chloride, extracted with ethyl acetate (4×100 ml). The organic extracts were collected, dried over sodium sulfate and concentrated to dryness to give 0.75 g of the product as a dark red oil.

EXAMPLE 8

4-[3-(4-(4-fluorobenzamido)piperidin)butoxy]-2-isopropylidenecumaran-3-one

A mixture of 4-(4chlorobutoxy)-2-isopropylidenecumaran-3-one (0.7 g; example 7), potassium carbonate (0.34 g) and 4-(4-fluorobenzamido)piperidine (0.72 g; preparation 2) in 10 ml of dimethylformamide was heated to 50° C. for 3 hours, then a further 0.25 g of 4-(4-fluorobenzamido)piperidine was added and stirring continued at 50° C. overnight.

The reaction mixture was poured into water (150 ml), sodium chloride was added and the mixture extracted with ethyl acetate (2×100 ml). The organic extracts were collected, washed with brine, dried over sodium sulfate and concentrated to dryness. The residue (1.5 g) was purified by silica gel chromatography (eluent chloroform/methanol 9:1), to give, after crystallization from diethyl ether/hexane, 0.17 g of the product, m.p. 150–154° C.

EXAMPLE 9

3-[4-(4-methylbenzamido) piperidinyl]-1-chloropropane

A mixture of 3-(4-aminopiperidin-1-yl)-1-chloropropane (1g; preparation 9), sodium carbonate (0.42 g) and toluoyl chloride (0.58 ml) in 20 ml of ethyl acetate and 20 ml of saturated aqueous sodium bicarbonate solution was stirred at room temperature for 3 hour, then poured into 100 ml of water. The organic phase was separated, dried over sodium sulfate and concentrated to dryness. The residue (1.4 g) was crystallized from 20 ml of hexane and the collected solid dried under vacuum at 50° C. to give 1.05 g of the product, m.p. 150–152° C.

EXAMPLE 10

4-[3-(4-(4-methylbenzamido)piperidinyl)propoxy]-2-isopropylidenecumaran-3-one

A mixture of 4-hydroxy-2-isopropylidenecumaran-3-one (0.61 g; preparation 3), 3-[4-(4-methylbenzamido) piperidinyl]-1-chloropropane (1.05 g; example 9) and potassium carbonate (0.44 g) in 15 ml of dry dimethylformamide was heated to 50° C. overnight, then cooled to room temperature and poured into 100 ml of water. The aqueous phase was extracted with chloroform (3×100 ml), then the organic extracts were pooled and washed with 50 ml of brine, dried over sodium sulfate and concentrated to dryness. The residue (7.5 g) was purified by silica gel chromatography (eluent chloroform(methanol/triethylamine 9:1:0.2) to give, after recrystallization from 15 ml of diethylether/hexane and drying under vacuum at 50° C., 0.95 g of the product, m.p. 198–202° C.

EXAMPLE 11

3-(4-benzamidopiperidinyl)-1-chloropropane

A mixture of 4-benzamidopiperidine (3.2 g; preparation I11), triethylamine (5.67 ml) and 1-bromo-3-chloropropane (2.31 ml) in 150 ml of tetrahydrofuran was refluxed overnight, then concentrated to a small volume and treated with 100 ml of chloroform. The solution was washed with 50 ml of aqueous saturated solution of potassium carbonate, dried over sodium sulfate and concentrated to dryness. The residue (6 g) was purified by silica gel chromatography (eluent chloroform/methanol 9:1) to give, after recrystallization from 20 ml of diethyl ether, 1.63 g of the product, m.p. 145–147° C.

EXAMPLE 12

4-[3-(4-benzamidotipyridinyl)propoxy]-2-isopropylidenecumaran-3-one 0.098 g of sodium metal was added to 50 ml of dry isopropanol and the mixture was kept at 60° C. until all of the sodium had dissolved. The reaction mixture was then treated with 0.67 g of 4-hydroxy-2-isopropylidenecumaran-3-one (preparation 3), refluxed for 30 minutes then treated with 3-(4-benzamidopiperidinyl)-1-chloropropane (1.01 g;

example 11) and again refluxed for a further 3 hours. The reaction mixture was concentrated to a small volume, treated with 100 ml of aqueous saturated potassium carbonate solution and extracted with ethyl acetate. The organic extracts were pooled, dried over sodium sulfate and concentrated to dryness. The residue (1.55 g) was purified by silica gel chromatography (eluent chloroform/methanol 15:1) to give, after recrystallization from ethyl acetate, 0.79 g of the product, m.p. 195–198° C.

EXAMPLE 13

4-[3-(4-(4-fluorobenzamido)piperidinyl)propoxy]-2-(4'-heptylidene)cumaran-3-one

A suspension of 0.11 g of sodium metal in 50 ml of dry isopropanol was heated at 60° C. until all of the sodium had dissolved, then a solution of 4-hydroxy-2-(4'-heptylidene) cumaran-3-one (1.02 g; preparation 12) in 50 ml of dry isopropanol was added and the reaction mixture refluxed for 30 minutes. 1.77 g of 3-[4(4-fluorobenzamido) piperidinyl]-1-chloropropane was then added. The mixture was heated to 80° C. for 4 hours, then poured in 150 ml of aqueous saturated potassium carbonate solution and extracted with ethyl acetate. The organic phase was dried over sodium sulfate and concentrated to dryness to give 2.3 g of an oily residue which was purified by silica gel column chromatography (eluent chloroform/methanol 9:2). After recrystallization from 20 ml of diethyl ether, 1.12 g of the product are obtained, m.p. 140–143° C.

EXAMPLE 14

2-[4-(4-fluorobenzamido)piperidinyl]-1-chloroethane

A mixture of 4-(4-fluorobenzamido)piperidine (2 g; preparation 2), triethylamine (3.75 ml) and 1-bromo-2-chloroethane (1.11 ml) in 150 ml of dry tetrahydrofuran was refluxed overnight, then further triethylamine (3.75 ml) and 1-bromo-2-chloroethane (1.11 ml) were added. The mixture was refluxed for an additional 5 hours, treated again with 3.75 ml of triethylamine and 1.11 ml of 1-bromo-2-chloroethane and refluxed overnight. The reaction mixture was concentrated to a small volume, treated with ethyl acetate (200 ml) and the mixture washed with an aqueous saturated potassium carbonate solution. The organic phase was dried over sodium sulfate and concentrated to dryness. The residue (1.3 g) was crystallized from 10 ml of diethyl ether and dried under vacuum at 50° C., to give 1.06 g of the product, m.p. 220–225° C.

EXAMPLE 15

4-[2-(4-(4-fluorobenzamido)piperidin)ethoxy]-2-isopropylidenecumaran-3-one

A suspension of 0.08 g of sodium metal in 50 ml of dry isopropanol was heated at 60° C. for 30 minutes (all of the sodium had then dissolved) and 0.55 g of 4-hydroxy-2-isopropylidene-cumaran-3-one (preparation 3) were added. After a further 30 minutes at reflux 1 g of 2-[4-(4-fluorobenzamido) piperidinyl]-1-chloroethane (example 14) was added and the reaction mixture refluxed for 4 hours. The solvent was evaporated under reduced pressure and the residue redissolved in 100 ml of methylene chloride and washed with 50 ml of aqueous saturated potassium carbonate solution. The organic phase was dried over sodium sulfate, concentrated to dryness and the residue (3 g of a red oil) purified by silica gel chromatography (eluent chloroform/methanol 9:1) to give, after crystallization from 10 ml of diethyl ether, 0.4 g of the product, m.p. 158–160° C.

EXAMPLE 16

3-(4-acetamidopiperidinyl)-1-chloropropane

A mixture of 4-acetamidopiperidine (1.4 g; preparation 14), triethylamine (3.56 ml) and 1-bromo-3-chloropropane (1.45 ml) in 50 ml of tetrahydrofuran was refluxed overnight, then an additional 3.5 ml of triethylamine and 1.45 ml of 1-bromo-3-chloropropane were added. After a further 3 hours at reflux, the mixture was concentrated to a small volume, treated with chloroform and washed with aqueous saturated solution of potassium carbonate. The organic phase was dried over sodium sulfate, concentrated to dryness and the residue (2.3 g of a green oil) was purified by silica gel chromatography (eluent chloroform/methanol 9:1) to give 0.67 g of the product, m.p. 74–77° C.

EXAMPLE 17

4-[3-(acetamidopiperidinyl)propoxy]-2-isopropylidenecumaran-3-one

A suspension of 0.07 g of sodium metal in 50 ml of dry isopropanol was heated to 60° C. until all of the sodium had dissolved, then 0.47 g of 4-hydroxy-2-isopropylidenecumaran-3-one (preparation 3) was added and the mixture refluxed for 30 minutes. 3-(4-acetamidopiperidinyl)-1-chloropropane (0.6 g; example 16) was then added and the reaction mixture again refluxed for 6 hours and finally concentrated to dryness. The residue was treated with 100 ml of chloroform and washed with 50 ml of aqueous saturated potassium carbonate solution. The organic phase was dried over sodium sulfate and concentrated to dryness and the residue (1.1 g of a red oil) purified by silica gel chromatography (eluent chloroform/methanol 9:1) to give, after crystallization from diethyl ether and drying under vacuum at 50° C., 0.48 g of the product, m.p. 150–153° C.

EXAMPLE 18

3-(4-heptanoylaminopiperidine-1-yl)-1-chloropropane

A mixture of 4-heptanoylaminopiperidine (7.49 g; preparation 16), triethylamine (9.79 ml) and 1-bromo-3-chloropropane (5.38 ml) in 200 ml of dry tetrahydrofuran was refluxed for 4 hours, then a further 9.79 ml of triethylamine and 5.38 ml of 1-bromo-3-chloropropane were added. The reaction mixture was refluxed overnight, then concentrated to dryness, treated with 100 ml of saturated aqueous potassium carbonate solution and extracted with ethyl acetate (2×100 ml). The organic extracts were pooled, dried over sodium sulfate and concentrated to dryness to give 15 g of an oil which was purified by silica gel chromatography (eluent chloroformlmethanol 9:1) to give, after crystallization from 30 ml of hexane, 6.12 g of the product, m.p. 68–70° C.

EXAMPLE 19

4-[3-(4-heptanoylaminopiperidine-1-yl)propoxy]-2-isopropylidenecumaran-3-one 0.1 g of sodium metal in 50 ml of dry isopropanol was heated to 60° C. until all of the sodium had dissolved, then 0.7 g of 4-hydroxy-2-isopropylidenecumaran-3-one (preparation 3) was added and the mixture refluxed for 30 minutes. 3-(4-heptanoylaminopiperidine-1-yl)-1-chloropropane (0.7 g; example 18) was then added and the reaction mixture refluxed overnight. The mixture was then concentrated to dryness, redissolved in methylene chloride, washed with 100 ml of saturated aqueous potassium carbonate solution, dried over sodium sulfate and concentrated to dryness. The residue (2 g) was purified by silica gel chromatography (eluent methylene chloride/methanol 9:1) to give, after crystallization from 20 ml of diethyl ether, 0.5 g of the product, m.p. 151–153° C.

EXAMPLE 20

4-[3-(4-(4-fluorobenzamido)piperidin-1-yl)propoxy]-2-cyclopentylidenecumaran-3-one A mixture of 4-hydroxy-2-cyclopentylidenecumaran-3-one (0.89 g; preparation 17), 3-[4-(4-fluorobenzamido)piperidinyl]-1-chloropropane (1.23 g; example 1) and potassium carbonate (0.56 g) in 10 ml of dry dimethylformamide was heated to 60° C. for 6 hours. The reaction mixture was then poured into 200 ml of water and the solid which separated recovered by filtration and purified by silica gel chromatography (eluent chloroform/methanol 9:1). The residue was crystallized from 20 ml of diethyl ether and dried under vacuum at 40° C., to give 0.45 g of the product, m.p. 160–162° C.

EXAMPLE 21

3-(4-cyclohexylamidopiperidine-1-yl)-1-chloropropane

A mixture of 4-cyclohexylamidopiperidine (3 g; preparation 19), triethylamine (5.16 ml) and 1-bromo-3-chloropropane (2.1 ml) in 100 ml of tetrahydrofuran was refluxed overnight, then a further 5.16 ml of triethylamine and 2.1 ml of 1-bromo-3-chloropropane were added. The mixture was refluxed for an additional 4 hours, then concentrated to a small volume, treated with 100 ml of saturated aqueous potassium carbonate solution and extracted with 100 ml of chloroform. The organic phase was dried over sodium sulfate and concentrated to dryness and the residue (8 g) recrystallized from 50 ml of diethyl ether to give 2.43 g of the product, m.p. 152–155° C.

EXAMPLE 22

4-[3-(4-cyclohexylamidopiperidine-1-yl)propoxy]-2-isopropylidenecumaran-3-one 0.09 g of sodium metal is 50 ml of dry isopropanol was heated to 60° C. until all of the sodium had dissolved, then 0.63 g of 4-hydroxy-2-isopropylidenecumaran-3-one (preparation 3) was added and the reaction mixture refluxed for 30 minutes. 3-(4-cyclohexylamidopiperidine-1-yl)-1-chloropropane (1.43 g; example 21) was then added and the mixture refluxed for an additional 5 hours, then concentrated to dryness and redissolved in 100 ml of chloroform. The resulting organic phase was washed with 50 ml of saturated aqueous potassium carbonate solution, dried over sodium sulfate and concentrated to dryness. The residue (2 g) was purified by silica gel chromatography (eluent chloroform/methanol 9:1) to give, after crystallization from a little ethyl acetate, 0.65 g of the product, m.p. 193–196° C.

Elem. Anal. (calcd/found %): C 70.88/67.70; H 8.24/8.22; 6.36/6.30.

EXAMPLE 23

According to the methods described in the previous preparations and examples, starting from the appropriate reactants, the following benzocumaranones were prepared:

4-[3-(4-nicotinamidopiperidin-1-yl)propoxy]-2-isopropylidenecumaran-3-one, m.p. 187–191° C.;

4-[3-(4-(4-trifluorometanbenzamido)piperidin-1-yl)propoxy]-2-isopropylidenecumaran-3-one, m.p. 191–193° C.;

4-[3-(4-(2-naphthoylamido)piperidin-1-yl)propoxy]-2-isopropylidenecumaran-3-one, m.p. 160–162° C.;

4-[3-(4-(3,4,5-trimethoxybenzamido)piperidin-1-yl)propoxy]-2-isopropylidenecumaran-3-one, m.p. 195–198° C.;

4-[3-(4-(4-bromobenzamido)piperidin-1-yl)propoxy]-2-isopropylidenecumaran-3-one, m.p. 176–179° C.;

4-[3-(4-(2-(O-phenoxy)acetamido)piperidin-1-yl)propoxy]- 2-isopropylidenecumaran-3-one, m.p. 115–118° C.;

4-[3-(4-(4-methoxybenzamido)piperidin-1-yl)propoxy]-2-isopropylidenecumaran-3-one, m.p. 148–151° C.;

4-[3-(4-(4-cyanobenzamido)piperidin-1-yl)propoxy]-2-isopropylidenecumaran-3-one, m.p. 175–178° C.;

4-[3-(4-(2-(3-indolyl)acetamido)piperidin-1-yl)propoxy]-2-isopropylidenecumaran-3-one, m.p. 196–201° C. (dec.);

4-[3-(4-(2-(phenyl)acetamido)piperidin-1-yl)propoxy]-2-isopropylidenecumaran-3-one, m.p. 139–142° C.;

4-[3-(4-(2-thenoylamido)piperidin-1-yl)propoxy]-2-isopropylidenecumaran-3-one, m.p. 215–218° C.;

4-[3-(4-(2-(4-fluorobenzamido)ethyl)piperidin-1-yl)propoxy]-2-isopropylidenecumaran-3-one, m.p. 151–153° C.;

(E)-4-[4-(4-(4-fluorobenzamido)piperidin-1-yl)-2-butenoxy]-2-isopropylidenecumaran-3-one, m.p. 150–152° C.;

(Z)-4-[4-(4-(4-fluorobenzamido)piperidin-1-yl)-2-butenoxy]- 2-isopropylidenecumaran-3-one, m.p. 88–90° C.;

4-[3-(4-(4-methylbenzamido)piperazin-1-yl)propoxy] -2-isopropylidenecumaran-3-one;

4-[$^3$-(4-((4-fluorobenzamido)methylpiperidin-1-yl)propoxy]-2-isopropylidenecumaran-3-one, m.p. 175–179° C.;

4-[(5-(4-(4-fluorobenzamido)piperidin-1-yl)penityl)oxy]-2-isopropylidenecumaran-3-one, m.p. 135–137° C.;

4-[(3-(4–4-nitrobenzamido)piperidin-1-yl)propoxy]-2-isopropylidenecumaran-3-one, m.p. 223–225° C.;

4-[(3-(4-(2,5-dichlorobenzamido)piperidin-1-yl)propoxy]-2-isopropylidenecumaran-3-one, m.p. 130–133° C.;

4-[(3-(4-(4-(methylsulfonyl)benzamido)piperidin-1-yl)propoxy]-2-isopropylidene-cumaran-3-one, m.p. 220–222° C.;

4-[(3-(4-(4-methylbenzamido)piperidin-1-yl)propoxy]-2-isopropylidenecumaran-3-one, m.p. 198–202° C.;

4-[(3-(4-(4chlorobenzamido)piperidin-1-yl)propoxy]-2-isopropylidenecumaran-3-one, m.p. 204–205° C.;

4-[(4-(4-(3-bromobenzamido)piperidin-1-yl)butyl)oxy]-2-isopropylidenecumaran-3-one, m.p. 145–148° C.;

4-[(4-(4-(4-trifluorometanbenzamido)piperidin-1-yl)butyl)oxy]-2-isopropylidene-cumaran-3-one, m.p. 145–148° C.;

(+)-4-[(3-(4-(4-fluorobenzamido)piperidin-1-yl)-2-hydroxyprop-1-yl)oxy]- 2-isopropylidenecumaran-3-one, m.p. 207–209° C.;

4-[(3-(4-(4-acetylaminobenzamido)piperidin-1-yl)propoxy]-2-isopropylidenecumaran-3-one, m.p. 243–245° C.;

4-[(3-(4-(1-naphthoylamido)piperidin-1-yl)propoxy]-2-isopropylidenecumaran-3-one, m.p. 173–175° C.;

4-[(3-(4-(3,4-dichlorobenzamido)piperidin-1-yl)propoxy]-2-isopropylidenecumaran-3-one, m.p. 188–190° C.;

4-[(3-(4-(3,5-dichlorobenzamido)piperidin-1-yl)propoxy]-2-isopropylidenecumaran-3-one, m.p. 203–205° C.;

4-[(3-(4-(3,5-bis(trifluoromethyl)benzamido)piperidin-1-yl)propoxy]-2-isopropylidenecumaran-3-one, m.p. 170–172° C.;

(S)4-[(3-(4-(4-((2-amino-1-oxo-3-phenylpropyl)amino)piperidin- 1-yl)propoxy]-2-isopropylidenecumaran-3-one dihydrochloride, m.p. 215–217° C.;

4-[(3-(4-(2-(4-fluorobenzamido)ethyl)piperazin-1-yl)propoxy]-2-isopropylidenecumaran-3-one, m.p. 158–160° C.;

4-[(2-(4-(2-(4-fluorobenzamido)ethyl)piperazin-1yl)ethyl)oxy]-2-isopropylidenecumaran-3-one, m.p. 103–105° C.;

4-[(3-(4-(4-(methoxycarbonyl)benzamido)piperidin-1-yl)propoxy]-2-isopropylidenecumaran-3-one, m.p. 226–228° C.;

4-[(3-(4-(3-cyanobenzamido)piperidin-1-yl)propoxy]-2-isopropylidenecumaran-3-one, m.p. 188–190° C.;

4-[(2-(4-(phenylacetyl)piperazin-1-yl)ethyl)oxy]-2-isopropylidenecumaran-3-one, m.p. 108–110° C.;

(S)4[(2-(4-(2-amino-1-oxo-3-phenylpropyl)piperazin-1-yl)ethyl)oxy]-2-isopropylidenecumaran-3-one dihydrochloride, m.p. 160–163° C.;

4-[(3-(4-(4-(dimethylamino)benzamido)piperidin-1-yl)propoxy]-2-isopropylidenecumaran-3-one, m.p. 210–212° C.;

4-[(3-(4-(2-bromobenzamido)piperidin-1-yl)propoxy]-2-isopropylidenecumaran-3-one, m.p. 140–142° C.;

4-[(3-(4-(3-chloro-4-fluorobenzamido)piperidin-1-yl)propoxy]-2-isopropylidenecumaran-3-one, m.p. 188–190° C.;

4-[(4-(4-(3,4-dichlorobenzamido)piperidin-1-yl)butyl)oxy]-2-isopropylidenecumaran-3-one, m.p. 163–165° C.;

4-[(3-(4-(3,4-difluorobenzamido)piperidin-1-yl)propoxy]-2-isopropylidenecumaran-3-one, m.p. 206–208° C.;

4-[(3-(4-(2,3,4-trifluorobenzamido)piperidin-1-yl)propoxy]-2-isopropylidenecumaran-3-one, m.p. 168–170° C.;

4-[(3-(4-(3-aminosulfonyl-4-chlorobenzamido)piperidin-1-yl)propoxy]-2-isopropylidenecumaran-3-one, m.p. 255–258° C.;

4-[(3-(4-(3-bromo-4-fluorobenzamido)piperidin-1-yl)propoxy]-2-isopropylidenecumaran-3-one, m.p. 206–208° C.;

4-[(6-(4-(4-fluorobenzamido)piperidin-1-yl)hexyl)oxy]-2-isopropylidenecumaran-3-one, m.p. 105–107° C.;

4-[(3-(4-(3-aminocarbonylbenzamido)piperidin-1-yl)propoxy]-²-isopropylidenecumaran-3-one, m.p. 154–156° C.;

(Z)4-[(4-(4-(3,4-dichlorobenzamido)piperidin-1-yl)but-2-en-1-yl)oxy]-2-isopropylidenecumaran-3-one, m.p. 155–158° C.;

(E)4-[(4-(4-(3,4-dichlorobenzamido)piperidin-1-yl)but-2-en1-yl)oxy]-2-isopropylidenecumaran-3-one, m.p. 179–181° C.;

4-[(3-(4-(2,4,5-trifluorobenzamido)piperidin-1-yl)propoxy]-2-isopropylidenecumaran-3-one, m.p. 156–158° C.;

4-[(2-((2-(4-(4-fluorobenzamido)piperidin-1-yl)ethyl)oxy)ethyloxy]-2-isopropylidenecumaran-3-one, m.p. 157.5–158.5° C.

What is claimed is:

1. A method of antagonizing the urokinase plasminogen activator receptor in a patient suffering from a solid tumor, or metastases thereof, comprising administering to the patient in need thereof a urokinase plasminogen activator receptor antagonizing amount of a compound of the formula (I):

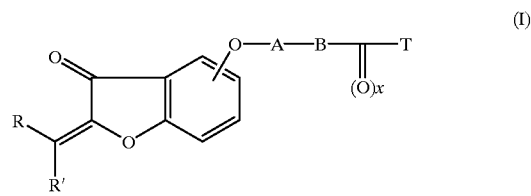

wherein:

R and R' are independently hydrogen, $C_{1-6}$-alkyl, styryl or $C_3$-cycloalkyl or, taken together with the carbon to which they are linked, form a $C_{3-6}$-cycloalkyl group;

x is 0 or 1;

A is —$(CH_2)_n$—, —$CH_2CH=CHCH_2$—, —$CH_2$—CH=CH—CH=CH—$CH_2$—, —$CH_2$—CH=CH—$CH_2$—$CH_2$—, —$CH_2$—$CH_2$—CH=CH—$CH_2$—, —$CH_2$—CH=CH—$CH_2$—$CH_2$—$CH_2$—, —$CH_2$—$CH_2$—CH=CH—$CH_2$—$CH_2$—, —$CH_2$—$CH_2$—CH=CH—$CH_2$—, —$CH_2$—CHOH—CHOH—$CH_2$—, —$(CH_2)_q$—O—$(CH_2)_q$, or —$CH_2$—A'—$CH_2$—, wherein q is an integer from 2 to 3 and n is an integer from 2 to 6, and A' is a $C_{3-7}$-cycloalkyl group;

B is

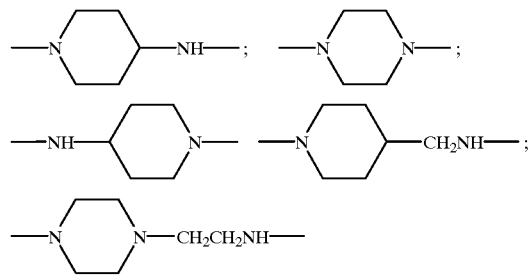

T is —$CH_2$—C≡CH, —C≡CH, —$(CH_2)_p$—$R^3$, —CH=CH—$R^3$, —$CH_2$—NHCO—$R^3$, —$(CH_2)_p$—O—$R^3$, or —CH(NH2)—$CH_2R^3$, in which p is 0 or an integer from 1to 4, $R^3$ is phenyl, naphthyl or biphenyl, unsubstituted or substituted by chlorine, bromine, iodine, fluorine, (C1–C6)alkyl, cyano, nitro, mono- or polyfluoroalkyl, —$SO_2(C_{1-4}$alkyl, —$SO_2NH_2$, —$SO_2NH(C_{1-4})$alkyl, —$SO_2N[(C_{1-4})$alkyl$]_2$, —$CONH_2$, —$CONH(C_{1-4})$alkyl, hydroxy, amino, carboxy, $C_{1-4}$-alkoxy, $(C_{1-4})$mono- or di-alkyl amino, $(C_{1-4})$alkoxycarbonyl, mercapto, or $C_{1-4}$-alkylthio, or is a 5- or 6-membered heterocycle which contains 1or 2 heteroatom(s) selected from oxygen, sulfur or nitrogen and which is or is not benzocondensed, or an enantiomer, diastereoisomer, or racemate of a compound of formula I, or a mixture thereof, or a pharmaceutically acceptable salt of a compound of formula I.

2. The method of claim 1, wherein the compound of formula I is (IA)

[Structure: benzofuranone with O—A—B—T substituent and R, R' groups, with (O)x]

wherein
R and R' are independently hydrogen, $C_{1-6}$-alkyl, styryl or $C_{3-6}$-cycloalkyl or, taken together with the carbon to which they are linked, form a $C_{3-6}$-cycloalkyl group;

x is 0 or 1;

A is —$(CH_2)_n$-, —$CH_2CH$=$CHCH_2$—, —$CH_2$—$CH$=$CH$—$CH$=$CH$—$CH_2$—, —$CH_2$—$CH$=$CH$—$CH_2$—$CH_2$—, —$CH_2$—$CH_2$—$CH$=$CH$—$CH_2$—, —$CH_2$—$CH$=$CH$—$CH_2$—$CH_2$—$CH_2$—, —$CH_2$—$CH_2$—$CH$=$CH$—$CH_2$—$CH_2$—, —$CH_2$—$CH_2$—$CH_2$—$CH$=$CH$—$CH_2$—, —$CH_2$—$CHOH$—$CHOH$—$CH_2$—, —$(CH_2)_q$—O—$(CH_2)_q$—, or —$CH_2$—A'—$CH_2$—, wherein q is an integer from 2 to 3 and n is an integer from 2 to 6, and A' is a $C_{3-7}$-cycloalkyl group;

B is

[Structures: piperidine-NH, piperazine, NH-piperidine-N, N-piperidine-CH₂NH, and N-piperazine-N-CH₂CH₂NH moieties]

T is —$CH_2$—$C$≡$CH$, —$CH$≡$CH$, —$(CH_2)_p$—$R^3$, —$CH$=$CH$—$R^3$, —$CH_2$—$NHCO$—$R^3$, —$(CH_2)_pO$—$R^3$, or —$CH(NH_2)$—$CH_2R^3$, in which p is 0 or an integer from 1 to 4, $R^3$ is phenyl, naphthyl or biphenyl, unsubstituted or substituted by chlorine, bromine, iodine, fluorine, (C1–C6)alkyl, cyano, nitro, mono- or polyfluoroalkyl, —$SO_2(C_{1-4})$alkyl, —$SO_2NH_2$, —$SO_2NH(C_{1-4})$alkyl, —$SO_2N[(C_{1-4})$alkyl$]_2$, —$CONH_2$, —$CONH(C_{1-4})$alkyl, hydroxy, amino, carboxy, $C_{1-4}$-alkoxy, $(C_{1-4})$mono- or di-alkyl amino, $(C_{1-4})$alkoxycarbonyl, mercapto, or $C_{1-4}$-alkylthio, or is a 5- or 6-membered heterocycle which contains 1or 2 heteroatom(s) selected from oxygen, sulfur or nitrogen and which is or is not benzocondensed, or an enantiomer, diastereoisomer, or racemate of a compound of formula IA or mixtures thereof, or a pharmaceutically acceptable salt of a compound of formula IA, with the proviso that when R and R' are both methyl, A is propyl, x is 1, and T is phenyl substituted by fluoro in the 4-position, B is not the moiety

[Structure: N-piperidine-NH]

3. The method of claim 2, wherein A is a —$(CH_2)_n$— group and n is an integer from 2–6, —$CH_2CH$=$CHCH_2$—, or —$(CH_2)_q$—O—$(CH_2)_q$— and q is an integer from 2 to 3.

4. The method of claim 2, wherein x is 1.

5. The method of claim 2, wherein B is the moiety

[Structure: N-piperidine-NH]

6. The method of claim 2, wherein T is phenyl or phenyl substituted by one or two trifluoro, bromo, chloro, fluoro, cyano, nitro, methyl or aminosulfonyl groups.

7. The method of claim 2, wherein R and R' are $C_{1-6}$—alkyl.

8. The method of claim 2, wherein x is 1, and B is the moiety

[Structure: N-piperidine-NH]

9. The method of claim 2, wherein R and R' are $C_{1-6}$-alkyl.

10. The method of claim 9, wherein A is a —$(CH_2)_n$— group and n is an integer from 2–6, —$CH_2CH$=$CHCH_2$—, or —$(CH_2)_q$—O—$(CH_2)_q$— and q is an integer from 2 to 3, and T is phenyl or phenyl substituted by one or two trifluoro, bromo, chloro, fluoro, cyano, nitro, methyl or aminosulfonyl groups.

11. The method of claim 10, wherein R and R' are methyl.

12. The method of claim 11, wherein A is a —$(CH_2)_n$— group and n is an integer from 2–6.

13. The method of claim 12, wherein n is an integer from 3–4.

14. The method of claim 13, wherein T is phenyl substituted by one or two trifluoro, bromo, chloro, fluoro, cyano, nitro, methyl or aminosulfonyl groups.

15. The method of claim 14, wherein the compound of formula IA is 4-(4-(4-(3,4-dichlorobenzamido)piperidin-1-yl)butoxy)-2-isopropylidenecumaran-3-one.

16. The method of claim 14, wherein the compound of formula IA is 4-(3-(4-(3-aminosulfonyl-4-chlorobenzamido)piperidin-1yl)propoxy)-2-isopropylidenecumaran-3-one.

17. The method of claim 11, wherein A is —$CH_2CH$=$CHCH_2$—.

18. The method of claim 17, wherein T is phenyl substituted by one or two trifluoro, bromo, chloro, fluoro, cyano, nitro, methyl or aminosulfonyl groups.

19. The method of claim 18, wherein the compound of formula IA is (E)-4-(4-(4-(3,4-dichlorobenzamido)piperidin-1-yl)-2-butenoxy)-2-isopropylidenecumaran-3-one.

20. The method of claim 18, wherein the compound of formula IA is (Z)-4-(4-(4-(3,4-dichlorobenzamido)piperidin-1-yl)-2-butenoxy)-2-isopropylidenecumaran-3-one.

21. The method of claim 11, wherein A is —(CH$_2$)$_q$—O—(CH$_2$)$_q$— and q is an integer from 2 to 3.

22. The method of claim 21, wherein T is phenyl substituted by one or two trifluoro, bromo, chloro, fluoro, cyano, nitro, methyl or aminosulfonyl groups.

23. The method of claim 22, wherein the compound of formula IA is 4-(4-(4-(4-fluorobenzamido)piperidin-1yl)ethoxyethoxy)-2-isopropylidenecumaran-3-one.

* * * * *

UNITED STATES PATENT AND TRADEMARK OFFICE
CERTIFICATE OF CORRECTION

PATENT NO. : 6,200,989 B1  
DATED : March 13, 2001  
INVENTOR(S) : Gianpiero De Cillis, Roberto Di Domenico, Bernhard König, Ambrogio Oliva Page 1 of 1

It is certified that error appears in the above-identified patent and that said Letters Patent is hereby corrected as shown below:

<u>Title page,</u>  
Item [75], Inventors, delete "Könic, Berg;" and insert -- König, Berg, Germany; --.

<u>Column 22, claim 1,</u>  
Line 32, delete "$C_3$-cycloalkyl" and insert -- $C_{3-6}$-cycloalkyl --.  
Line 65, delete "-$SO_2(C_{1-4}$alkyl," and insert -- -$SO_2(C_{1-4})$alkyl, --.

<u>Column 23, claim 1,</u>  
Line 1, delete "$(C_{1-4'})$alkoxycarbonyl," and insert -- $(C_{1-4})$alkoxycarbonyl, --.

<u>Column 24, claim 9,</u>  
Line 34, delete "2," and insert -- 8, --.

Signed and Sealed this

Twenty-fifth Day of December, 2001

Attest:

*Attesting Officer*

JAMES E. ROGAN  
*Director of the United States Patent and Trademark Office*